United States Patent
Zang et al.

(10) Patent No.: US 10,689,432 B2
(45) Date of Patent: Jun. 23, 2020

(54) B7X AND ITS DERIVATIVES FOR TREATING AND PREVENTING CARDIOVASCULAR DISEASE

(71) Applicant: ALBERT EINSTEIN COLLEGE OF MEDICINE, Bronx, NY (US)

(72) Inventors: Xingxing Zang, New York, NY (US); Hyungjun Jeon, Fort Lee, NJ (US)

(73) Assignee: Albert Einstein College of Medicine, Bronx, NY (US)

( * ) Notice: Subject to any disclaimer, the term of this patent is extended or adjusted under 35 U.S.C. 154(b) by 201 days.

(21) Appl. No.: 15/100,995

(22) PCT Filed: Dec. 9, 2014

(86) PCT No.: PCT/US2014/069191
§ 371 (c)(1),
(2) Date: Jun. 2, 2016

(87) PCT Pub. No.: WO2015/094782
PCT Pub. Date: Jun. 25, 2015

(65) Prior Publication Data
US 2016/0304581 A1    Oct. 20, 2016

Related U.S. Application Data

(60) Provisional application No. 61/917,471, filed on Dec. 18, 2013.

(51) Int. Cl.
| | |
|---|---|
| *A61K 39/00* | (2006.01) |
| *C07K 14/705* | (2006.01) |
| *A61K 38/17* | (2006.01) |
| *G01N 33/566* | (2006.01) |
| *G01N 33/569* | (2006.01) |

(52) U.S. Cl.
CPC .... *C07K 14/70532* (2013.01); *A61K 38/1774* (2013.01); *G01N 33/566* (2013.01); *G01N 33/56972* (2013.01); *C07K 2319/30* (2013.01); *G01N 2333/705* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 2005/0163772 A1* | 7/2005 | Dong | C07K 14/70532 424/141.1 |
| 2010/0203056 A1 | 8/2010 | Irving et al. | |
| 2012/0207759 A1 | 8/2012 | Murphy et al. | |
| 2012/0276095 A1 | 11/2012 | Langermann et al. | |

OTHER PUBLICATIONS

Mallat et al., 2009, J. Lipid. Res. vol. 50: S364-S369.*
PCT International Search Report and Written Opinion, dated Mar. 9, 2015 in connection with PCT International Application No. PCT/US2014/069191, 10 pages.
Zeng C et al., entitled "BTLA, a New Inhibitory B7 Family Receptor with a TNFR Family Ligand," Cellular & Molecular Immunology, Dec. 1, 2005, vol. 2, No. 6, pp. 427-432.
Yamaura K et al., entitled "In Vivo Function of Immune Inhibitory Molecule B7-H4 in Alloimmune Responses," American Journal of Transplantation, 2010, vol. 10, pp. 2355-2362.

* cited by examiner

*Primary Examiner* — Amy E Juedes
(74) *Attorney, Agent, or Firm* — Perkins Coie LLP

(57) ABSTRACT

Methods are disclosed for preventing and/or treating cardiovascular diseases comprising administering B7x or a derivative of B7x to a patient in need thereof.

3 Claims, 4 Drawing Sheets
Specification includes a Sequence Listing.

B7X AND ITS DERIVATIVES FOR TREATING AND PREVENTING CARDIOVASCULAR DISEASE

CROSS-REFERENCE TO RELATED APPLICATIONS

This application is a U.S. national stage entry under 35 U.S.C. § 371 of PCT International Patent Application No. PCT/US2014/069191, filed Dec. 9, 2014, which claims the benefit of U.S. Provisional Patent Application No. 61/917,471, filed Dec. 18, 2013, the contents of which are incorporated herein by reference into the subject application.

STATEMENT OF GOVERNMENT SUPPORT

This invention was made with government support under grant number DK083076 awarded by the National Institutes of Health. The government has certain rights in the invention.

BACKGROUND OF THE INVENTION

Throughout this application various publications are referred to in superscripts. Full citations for these references may be found at the end of the specification. The disclosures of these publications are hereby incorporated by reference in their entirety into the subject application to more fully describe the art to which the subject invention pertains.

Atherosclerosis is an inflammatory disease of the arterial wall in which T cell- and other immune cell-mediated immunity play a significant component[8,9]. It is well known that atherosclerosis can lead to serious problems, including heart attack, stroke, or even death. Atherosclerosis can affect any artery in the body, such as arteries in the heart, brain, kidneys, legs, pelvis, and arms. As a consequence, different diseases can develop based on the arteries that are affected. More than 80 million Americans suffer from some form of cardiovascular disease including atherosclerosis[10]. Atherosclerosis related diseases include coronary heart disease (the number one killer of both men and women in the US), carotid artery disease, peripheral arterial disease and chronic kidney disease.

The B7 ligand family binds to the CD28 receptor family on T cells and other immune cells, which critically regulates functions of immune cells. The currently known members of the B7 family includes B7-1 (CD80), B7-2 (CD86), B7h (CD275), PD-L1 (B7-H1, CD274), PD-L2 (CD273), B7-H3 (CD276), B7x (B7-H4/B7s1) and HHLA2 (B7h7/B7-H5), whereas the CD28 family contains CD28, CTLA-4 (CD152), ICOS (CD278) and PD-1 (CD279)[1,2]. B7x is a member of the B7/CD28 families and inhibits T cell function[3]. B7x inhibits T cell functions through binding activated T cells and myeloid derived suppressor cells. Over-expression of B7x abrogates pancreas damage mediated by self-reactive CD4 and CD8 T cells in vivo[4-7].

The present invention addresses the serious and long-felt need for improved methods for preventing and/or treating cardiovascular diseases such as atherosclerosis using B7x and B7x derivatives.

SUMMARY OF THE INVENTION

Methods are provided for preventing a cardiovascular disease in a patient at risk for developing a cardiovascular disease and/or for treating a cardiovascular disease in a patient in need thereof comprising administering to the patient B7x or a B7x derivative in an amount effective to prevent and/or treat a cardiovascular disease in a patient.

Methods are also provided for screening for a compound that treats and/or prevents a cardiovascular disease in a patient, comprising determining whether or not a B7x derivative binds to a receptor on T cells, wherein a B7x derivative that binds to a receptor on T cells is a candidate compound for treating and/or preventing a cardiovascular disease, and testing the candidate compound to determine whether or not the candidate compound treats and/or prevents a cardiovascular disease.

Methods are further provided for screening for a compound that treats and/or prevents a cardiovascular disease in a patient, comprising obtaining a derivative of B7x, and testing whether or not the B7x derivative treats and/or prevents a cardiovascular disease.

DETAILED DESCRIPTION OF THE INVENTION

Figures 1A, 1B:
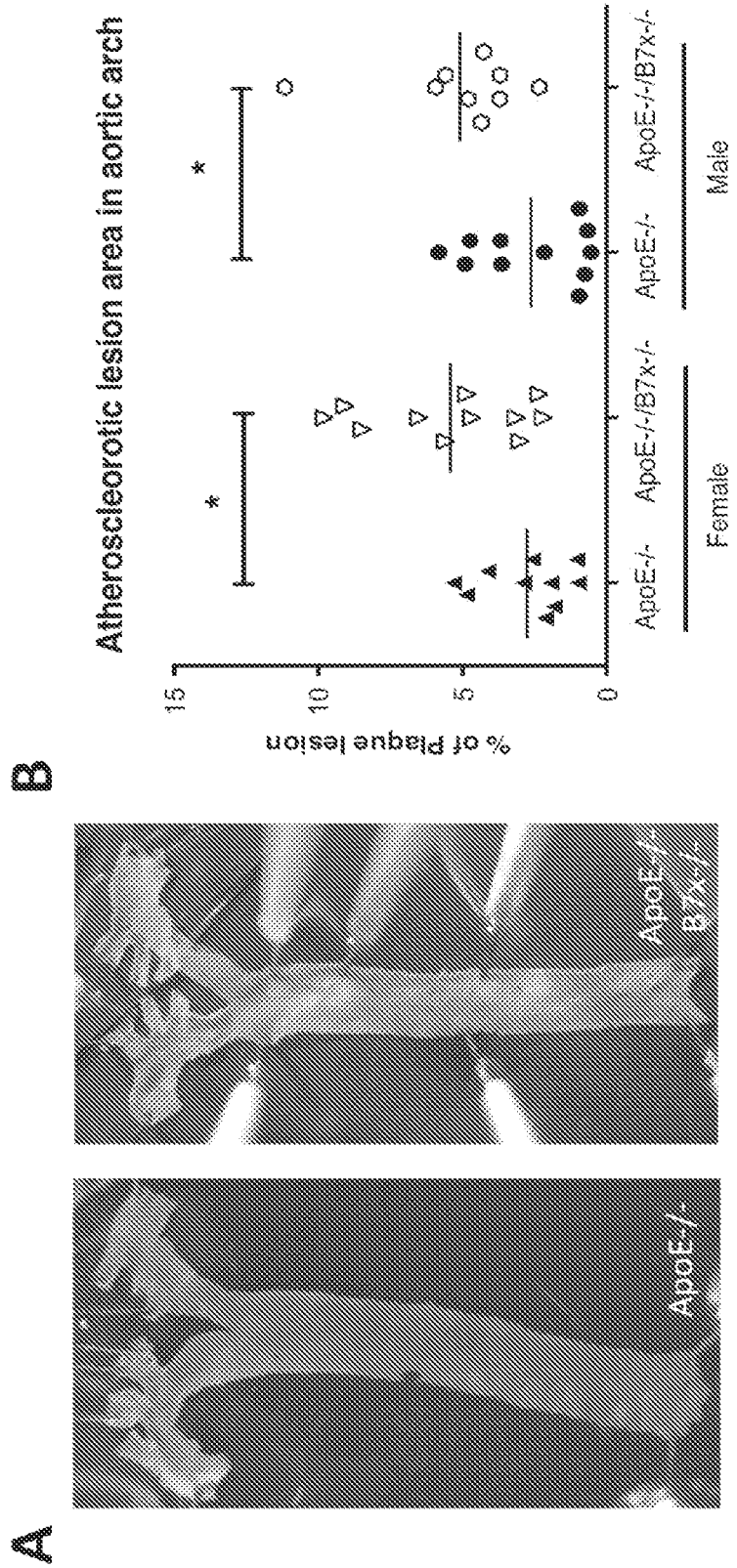
FIG. 1A-1B. B7x deficiency increases atherosclerotic burden. (A) Visibly different plaque sizes in aortic arch regions of representative high cholesterol diet-fed ApoE−/− and ApoE−/−B7x−/− mice. En face Oil red 0 staining was used to detect lipid-deposited plaque areas in aortas. Plaque areas stain red. (B) Quantitative comparison of percentages of plaque areas in the total aortic arch regions of high cholesterol diet-fed ApoE−/− and ApoE−/−B7x−/− mice. In both male and female mice, B7x deficiency led to more than 94% increase in plaque lesion. N=9-11, *P<0.05.

The invention provides a method of preventing a cardiovascular disease in a patient at risk for developing a cardiovascular disease and/or for treating a cardiovascular disease in a patient in need thereof comprising administering to the patient B7x (also called B7-H4 or B7S1) or a B7x derivative in an amount effective to prevent and/or treat a cardiovascular disease in a patient.

In one embodiment, B7x is administered to the patient. In another embodiment, a B7x derivative is administered to the patient. Examples of B7x derivatives, include, but are not limited to high-affinity mutants, low-affinity mutants, IgV domain of B7x fusion protein, fused to other molecules, etc. Preferred B7x derivatives include B7x Ig fusion proteins, such as, for example, the coding region of the extracellular domain of B7x fused to a human IgG1 fragment crystallizable region (Fc region), which can have the amino acid sequence SKTSGSEPKSCDKTHTCPPCPAPELLGGPSV-FLFPPKPKDTLMISRTPEVTCVVVDVS HEDPEVKFN-WYVDGVEVHNAKTKPREEQYNSTYRVVSVLTVL-HQDWLNGKEYK
CKVSNKALPAPIEKTISKAK-
GQPREPQVYTLPPSREEMTKNQVSLTCLVKGFYPSDI AVEWESNGQPENNYKTTPPVLDSDGSFFLYSKLT-VDKSRWQQGNVFSCSVMHEAL HNHYTQK-SLSLSPGK (SEQ ID NO:3).

The patient can have a cardiovascular disease. To "treat" a cardiovascular disease means to reduce or eliminate a sign or symptom of the cardiovascular disease.

The patient can be at risk for developing a cardiovascular disease. Patients at risk for developing a cardiovascular disease include subjects diagnosed with a genetic predeposition for a cardiovascular disease, subjects diagnosed with a cholesterol and/or triglicaride or other biological profile that indicates that the subject is at risk for developing a cardiovascular disease, and patients with a history of cardiovascular disease.

The invention also provides a method of screening for a compound that treats and/or prevents a cardiovascular disease in a patient, the method comprising determining whether or not a B7x derivative binds to a receptor on T cells, wherein a B7x derivative that binds to a receptor on T cells is a candidate compound for treating and/or preventing a cardiovascular disease, and testing the candidate compound to determine whether or not the candidate compound treats and/or prevents a cardiovascular disease.

The invention further provides a method for screening for a compound that treats and/or prevents a cardiovascular disease in a patient, the method comprising obtaining a derivative of B7x, and testing whether or not the B7x derivative treats and/or prevents a cardiovascular disease.

The cardiovascular disease can be, for example, atherosclerosis, coronary heart disease, carotid artery disease, peripheral arterial disease, or chronic kidney disease.

Preferably, the patient or subject is a human.

Human and mouse B7x have the amino acid sequences indicated below.

```
Human B7x amino acid sequence (SEQ ID NO: 1):
MASLGQILFWSIISIIIILAGAIALIIGFGISGRHSITVTTVASAGNIGE

DGILSCTFEPDIKLSDIVIQWLKEGVLGLVHEFKEGKDELSEQDEMFRGR

TAVFADQVIVGNASLRLKNVQLTDAGTYKCYIITSKGKGNANLEYKTGAF

SMPEVNVDYNASSETLRCEAPRWFPQPTVVWASQVDQGANFSEVSNTSFE

LNSENVTMKVVSVLYNVTINNTYSCMIENDIAKATGDIKVTESEIKRRSH

LQLLNSKASLCVSSFFAISWALLPLSPYLMLK
```

```
Mouse B7x amino acid sequence (SEQ ID NO: 2):
MASLGQIIFWSIINIIIILAGAIALIIGFGISGKHFITVTTFTSAGNIGE

DGTLSCTFEPDIKLNGIVIQWLKEGIKGLVHEFKEGKDDLSQQHEMFRGR

TAVFADQVVVGNASLRLKNVQLTDAGTYTCYIRTSKGKGNANLEYKTGAF

SMPEINVDYNASSESLRCEAPRWFPQPTVAWASQVDQGANFSEVSNTSFE

LNSENVTMKVVSVLYNVTINNTYSCMIENDIAKATGDIKVTDSEVKRRSQ

LQLLNSGPSPCVFSSAFVAGWALLSLSCCLMLR.
```

This invention will be better understood from the Experimental Details, which follow. However, one skilled in the art will readily appreciate that the specific methods and results discussed are merely illustrative of the invention as described more fully in the claims that follow thereafter.

Experimental Details

B7x Deficiency Leads to Markedly Increased Atherosclerosis Progression In Vivo.

Figures 2A, 2B:
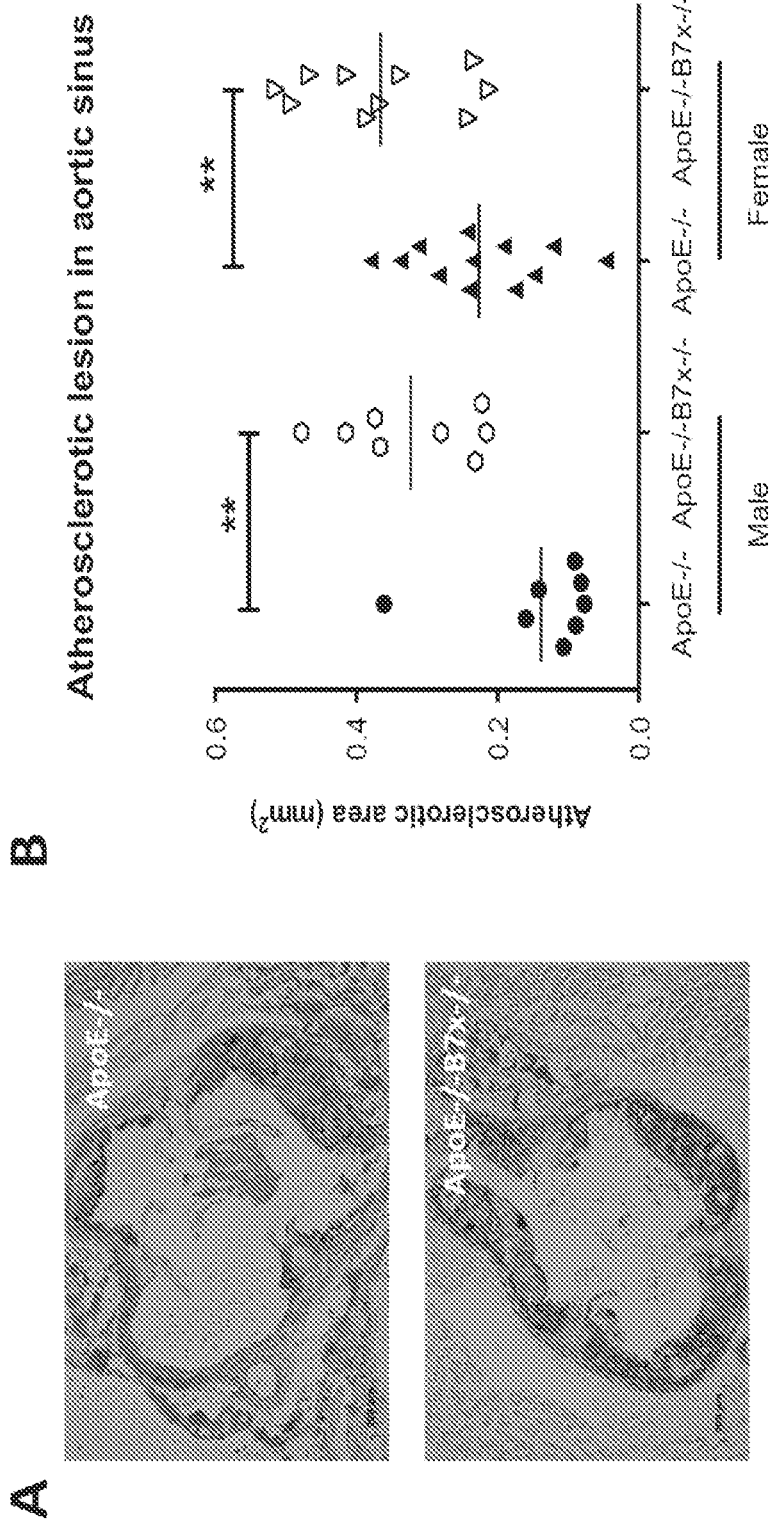
FIG. 2A-2B. B7x deficiency increases atherosclerotic plaque lesions in aortic sinus. (A) Representative cross sections of the Oil red 0-stained aortic sinuses of high cholesterol diet-fed ApoE−/− and ApoE−/−B7x−/− mice. (B) Quantitative comparison of atherosclerotic areas in the aortic sinus regions of high cholesterol diet-fed ApoE−/− and ApoE−/−B7x−/− mice. In male mice, B7x deficiency led to more than 133% increase in plaque lesion in aortic sinus regions; in female mice, B7x deficiency led to more than 61% increase in plaque lesion in aortic sinus regions; N=8-12, **P<0.01.
Figures 3A, 3B:
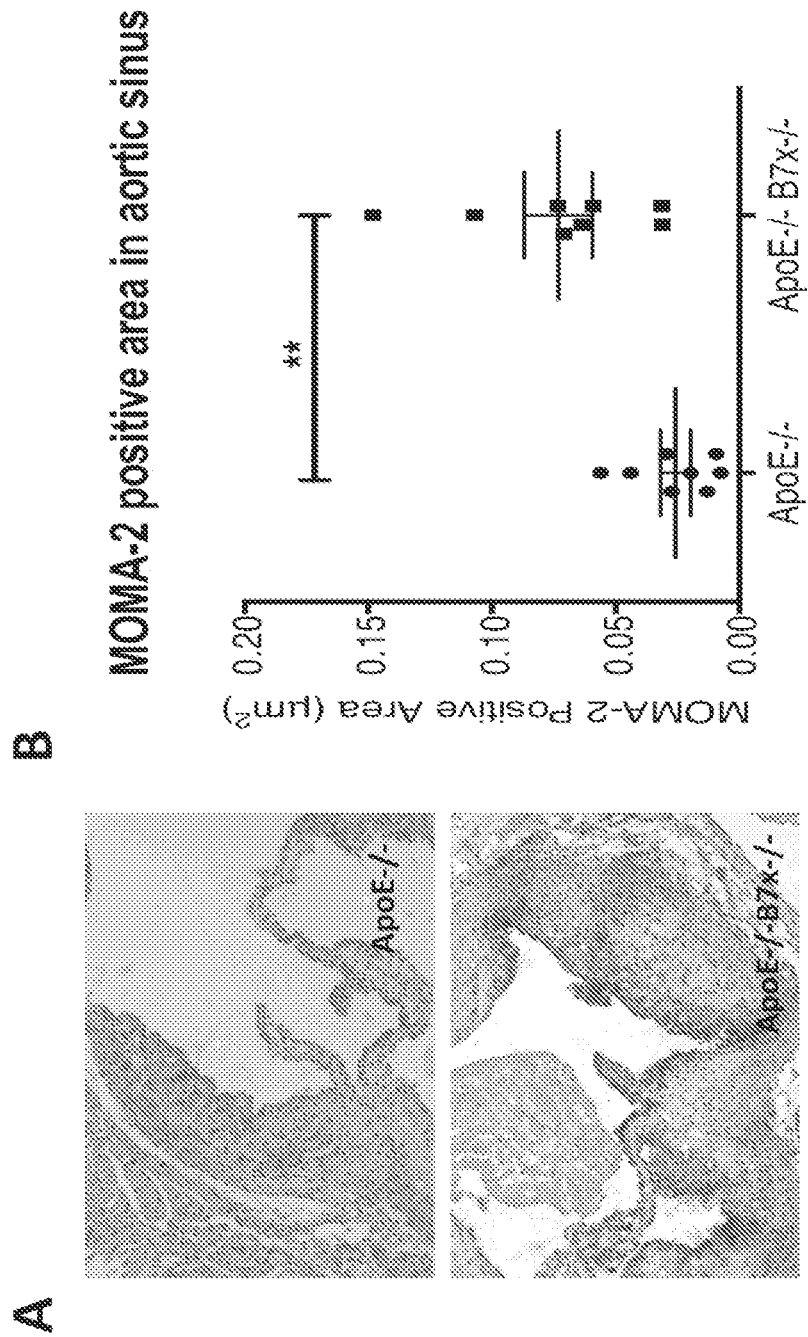
FIG. 3A-3B. B7x deficiency increases monocytes/macrophages positive area in the atherosclerotic lesions. (A) Representative cross sections of aortic sinuses where monocytes/macrophages were stained by anti-MOMA2 antibody from high cholesterol diet-fed ApoE−/− and ApoE−/−B7x−/− mice. (B) Quantitative comparison of monocytes/macrophages positive areas in the aortic sinus regions of high cholesterol diet-fed ApoE−/− and ApoE−/−B7x−/− mice. B7x deficiency led to more than 292% increase in monocytes/macrophages positive areas in aortic sinus regions; N=8, **P<0.01.

The role of B7x in atherosclerosis was completely unknown until the present invention. The role of the B7x pathway in atherosclerosis was examined in vivo. B7x gene knock-out mice (B7x−/−) on the C57Bl/6 background were crossed to ApoE−/− mice on the C57Bl/6 background to generate ApoE−/−B7x−/− mice. Sex- and age-matched ApoE−/− and ApoE−/−B7x−/− mice were fed with high cholesterol diet for eight weeks to induce atherosclerosis. ApoE−/−B7x−/− mice developed more severe atherosclerosis than ApoE−/− mice. The comparison of percentages of atherosclerotic plaque areas in the total aortic arch regions showed that both male and female ApoE−/−B7x−/− mice had more than 94% increase in plaque lesion than ApoE−/− mice (FIG. 1, P<0.05). Male and female ApoE−/−B7x−/− mice had more than 133% and 61% increase in plaque lesion in aortic sinus regions than male and female ApoE−/− mice (FIG. 2, P<0.01), respectively. ApoE−/−B7x−/− mice had more than a 292% increase in monocytes/macrophages positive areas in aortic sinus regions than ApoE−/− mice after a high cholesterol diet for eight weeks (FIG. 3, P<0.01). Together, these results demonstrate that the loss of B7x results in exacerbated atherosclerosis disease and that the B7x pathway has an important role in down-regulating atherosclerosis.

B7x-Ig Protein Significantly Inhibits Atherosclerosis Progression In Vivo.

Figure 4:
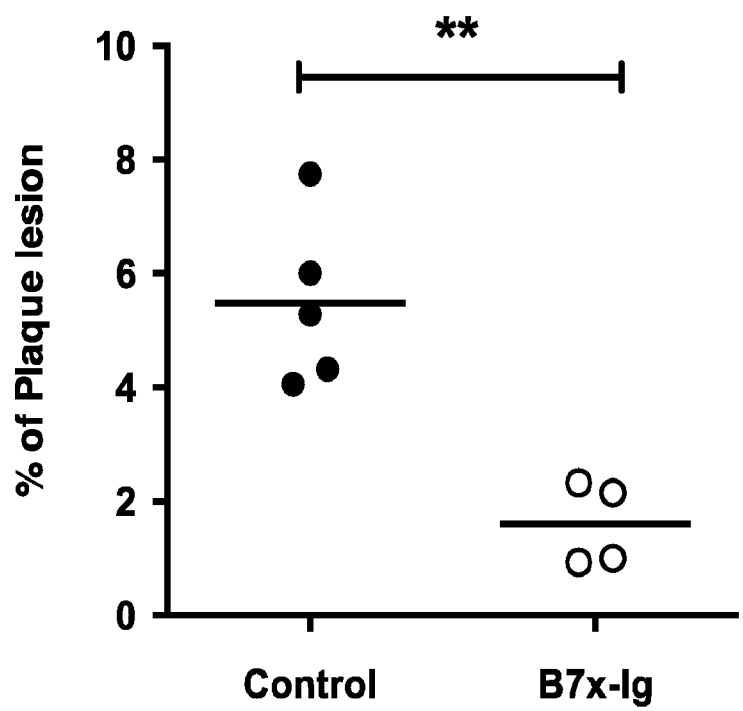
FIG. 4. B7x-Ig protein significantly inhibits atherosclerosis progression in vivo. ApoE−/− mice were fed with high cholesterol diet for eight weeks to induce atherosclerosis. During the first week mice were iv injected with 400 μg B7x-Ig or the control. The percentages of plaque areas in the total aortic arch regions were examined. B7x-Ig treatment reduced more than 70% of the atheroscleorotic lesion; N=4-5, **P<0.01.

Given that B7x-Ig protein can inhibit in vitro function of both mouse and human T cells[2,3] and that B7x deficiency leads to markedly increased atherosclerosis progression in vivo (FIG. 1-3), B7x-Ig was used to treat atherosclerosis in vivo. ApoE−/− mice were fed with high cholesterol diet for eight weeks to induce atherosclerosis. During the first week mice were iv injected with 400 μg B7x-Ig or control and the percentages of plaque areas in the total aortic arch regions were examined after eight weeks. B7x-Ig treatment reduced more than 70% of the atheroscleorotic lesion (FIG. 4, P<0.01), suggesting that B7x-Ig protein significantly inhibits atherosclerosis progression in vivo.

Mechanisms of the Present Treatment for Atherosclerosis and Related Cardiovascular Diseases.

There are at least two possible mechanisms by which B7x-Ig treatment inhibits atherosclerosis progression in vivo: (A) B7x-Ig binds activated T cells and inhibits proliferation and function of these T cells, thereby decreasing T cell-mediated immune responses and inflammation in atherosclerosis; and (B) B7x-Ig binds immune suppressor cells (myeloid derived suppressor cells, regulatory T cells, etc.) and stimulates their generation and/or immunosuppressive function, thereby decreasing immune response and inflammation in atherosclerosis.

The present studies have demonstrated that the B7x pathway has an important role in down-regulating atherosclerosis and that B7x-Ig fusion protein can be used as a new drug to treat and/or prevent atherosclerosis and related cardiovascular diseases such as coronary heart disease (the number one killer of both men and women in the US), carotid artery disease, peripheral arterial disease, chronic kidney disease, etc. Derivatives of B7x protein (such as high-affinity mutants or low-affinity mutants, IgV domain of B7x fusion protein, fused to other molecules, etc.) can be used as new drugs to treat and/or prevent atherosclerosis and related cardiovascular diseases such as coronary heart disease, carotid artery disease, peripheral arterial disease, chronic kidney disease, etc.

REFERENCES

1. Scandiuzzi, L., Ghosh, K. & Zang, X. T cell costimulation and coinhibition: genetics and disease. *Discov Med* 12, 119-128 (2011).
2. Zhao, R., et al. HHLA2 is a member of the B7 family and inhibits human CD4 and CD8 T-cell function. *Proc Natl Acad Sci USA* 110, 9879-9884 (2013).
3. Zang, X., et al. B7x: a widely expressed B7 family member that inhibits T cell activation. *Proc Natl Acad Sci USA* 100, 10388-10392 (2003).
4. Wei, J., Loke, P., Zang, X. & Allison, J. P. Tissue-specific expression of B7x protects from CD4 T cell-mediated autoimmunity. *The Journal of experimental medicine* 208, 1683-1694 (2011).
5. Lee, J. S., et al. B7x in the periphery abrogates pancreas-specific damage mediated by self-reactive CD8 T cells. *J Immunol* 189, 4165-4174 (2012).
6. Abadi, Y. M., et al. Host b7x promotes pulmonary metastasis of breast cancer. *J Immunol* 190, 3806-3814 (2013).
7. Jeon, H., Ohaegbulam, K. C., Abadi, Y. M. & Zang, X. B7x and myeloid derived suppressor cells in the tumor microenvironment: A tale of two cities. *OncoImmunology* 2, e247441-247443 (2013).
8. Frostegard, J. Immunity, atherosclerosis and cardiovascular disease. *BMC Med* 11, 117 (2013).
9. Keaney, J. F., Jr. Immune modulation of atherosclerosis. *Circulation* 124, e559-560 (2011).
10. Go, A. S., et al. Heart disease and stroke statistics—2013 update: a report from the American Heart Association. *Circulation* 127, e6-e245 (2013).

What is claimed is:

1. A method of inhibiting atherosclerosis progression in a patient comprising administering to the patient a B7x derivative in an amount and manner effective to inhibit atherosclerosis progression in a patient, wherein the B7x derivative is a B7x Ig fusion protein that comprises the extracellular domain of B7x fused to a human IgG1 fragment crystallizable region having the amino acid sequence (SEQ ID NO: 3)
SKTSGSEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSREEMT

KNQVSLTCLVKGFYPSDIAVEWESNGQPENNYKTTPPVLDSDGSFFLYSK

LTVDKSRWQQGNVFSCSVMHEALHNHYTQKSLSLSPGK.

2. The method of claim 1, wherein the patient is a human.

3. The method of claim 1, wherein the B7x Ig fusion protein is administered in an amount and manner effective to reduce an atherosclerotic lesion in a patient.

* * * * *

```
SEQUENCE LISTING

<160> NUMBER OF SEQ ID NOS: 3

<210> SEQ ID NO 1
<211> LENGTH: 282
<212> TYPE: PRT
<213> ORGANISM: Homo sapiens

<400> SEQUENCE: 1

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190
```

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
            210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
            245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
            275                 280

<210> SEQ ID NO 2
<211> LENGTH: 283
<212> TYPE: PRT
<213> ORGANISM: Mus musculus

<400> SEQUENCE: 2

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Phe Thr Ser Ala Gly Asn Ile
            35                  40                  45

Gly Glu Asp Gly Thr Leu Ser Cys Thr Phe Glu Pro Asp Ile Lys Leu
50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
            85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
            115                 120                 125

Thr Cys Tyr Ile Arg Thr Ser Lys Gly Lys Gly Asn Ala Asn Leu Glu
            130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
            165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
            210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
            245                 250                 255

Gly Pro Ser Pro Cys Val Phe Ser Ala Phe Val Ala Gly Trp Ala
            260                 265                 270

Leu Leu Ser Leu Ser Cys Cys Leu Met Leu Arg

-continued

```
                    275                 280

<210> SEQ ID NO 3
<211> LENGTH: 238
<212> TYPE: PRT
<213> ORGANISM: Homo sapiens

<400> SEQUENCE: 3

Ser Lys Thr Ser Gly Ser Glu Pro Lys Ser Cys Asp Lys Thr His Thr
1               5                   10                  15

Cys Pro Pro Cys Pro Ala Pro Glu Leu Leu Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235
```